United States Patent [19]

Gilbertson et al.

[11] Patent Number: 5,064,431
[45] Date of Patent: Nov. 12, 1991

[54] ANNULOPLASTY RING

[75] Inventors: Charles H. Gilbertson, Mendota Heights; William S. Nettekoven, Stillwater; Mark W. Cater, St. Louis Park, all of Minn.

[73] Assignee: St. Jude Medical Incorporated, St. Paul, Minn.

[21] Appl. No.: 641,914

[22] Filed: Jan. 16, 1991

[51] Int. Cl.$^5$ .............................. A61F 2/24; A61F 2/02
[52] U.S. Cl. ............................................ 623/2; 623/11
[58] Field of Search ................. 623/2, 11, 12, 66, 900

[56] References Cited

U.S. PATENT DOCUMENTS

| | | | |
|---|---|---|---|
| 4,042,979 | 8/1977 | Angell | 623/2 |
| 4,290,151 | 9/1981 | Massana | 623/2 |
| 4,489,446 | 12/1984 | Reed | 623/2 |

Primary Examiner—Ronald Frinks
Attorney, Agent, or Firm—Leydig, Voit & Mayer

[57] ABSTRACT

An annuloplasty ring of a tubular construction having two drawstrings, the ends of which extend from openings in the tube. The ring tube is stitched through the mid-section, defining two channels, the inner of which carries the drawstrings, and outer of which is used as a sewing flange for suturing the ring in place. A colored line along the top and bottom of the ring marks the stitching line, and, therefore, the dividing line between the channels. Each of the drawstrings is anchored at two anchor points, the anchor points alternating around the circumference of the ring to create a fixed non-adjustable zone between the center anchor points, two transitional adjustable zones, between the outside anchor point pairs, each being controlled by one or the other of the drawstrings, and two adjustable zones between the outermost anchor points and the openings in the tube from which the drawstrings extend, each being controlled by both drawstrings, such that the drawstrings may be uniformly or selectively, symmetrically or asymmetrically tightened to adjust the annulus to a desired shape.

16 Claims, 1 Drawing Sheet

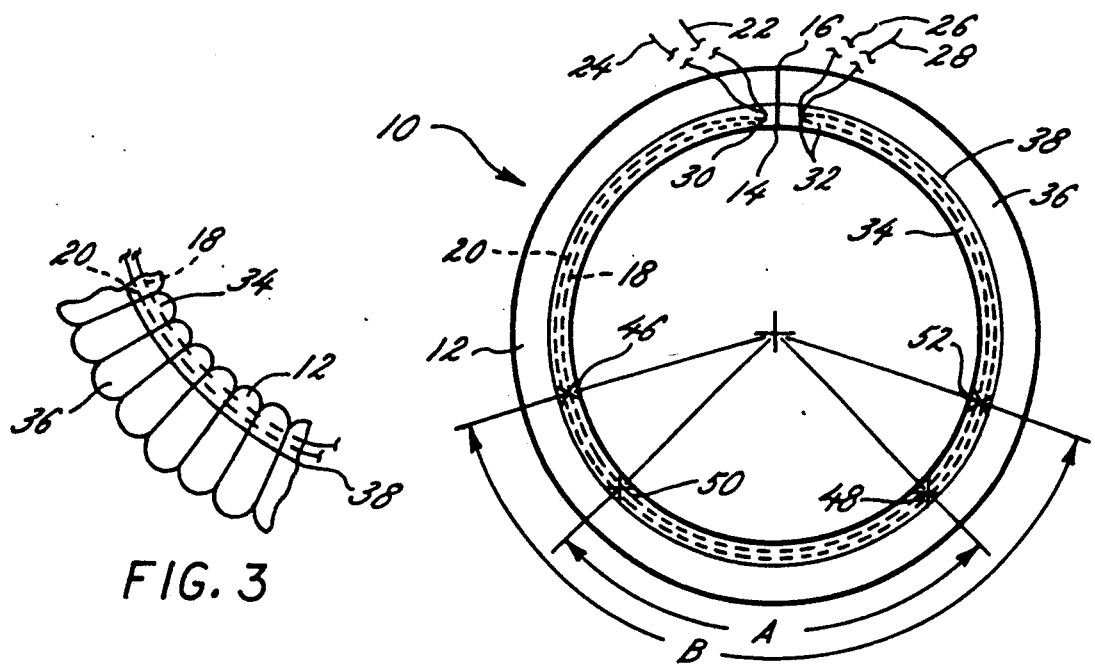
FIG. 3
FIG. 1
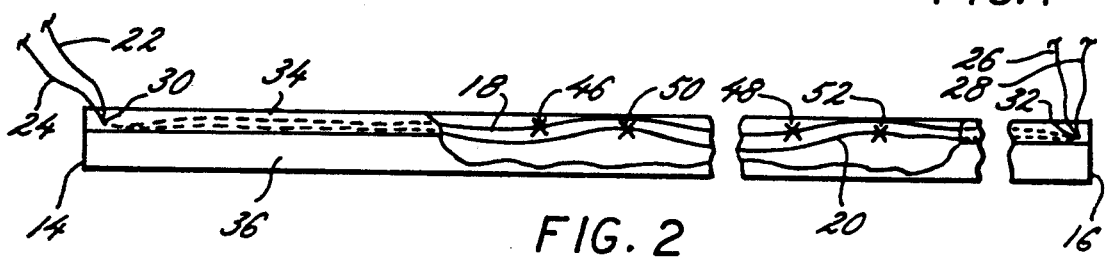
FIG. 2
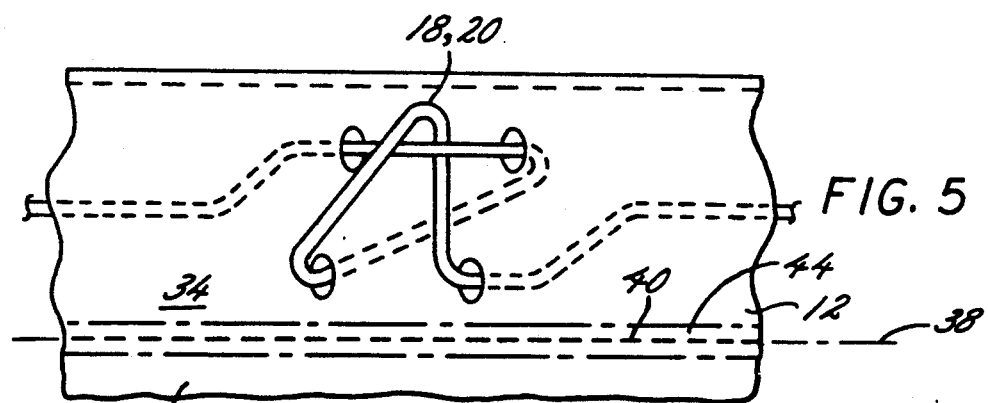
FIG. 5
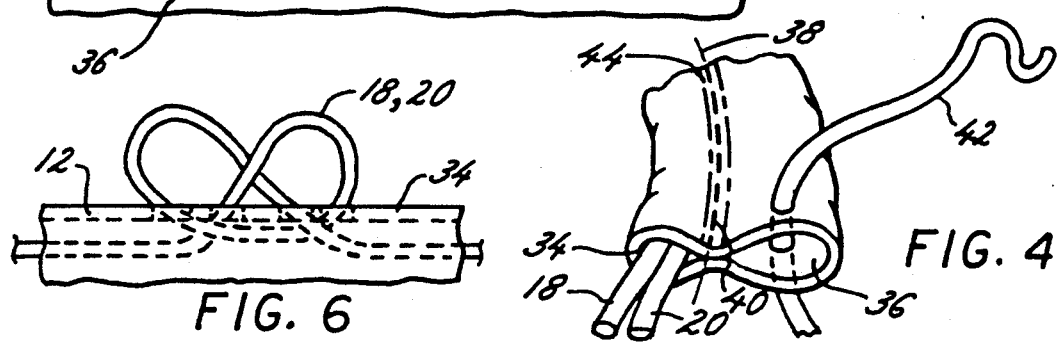
FIG. 6
FIG. 4

ANNULOPLASTY RING

FIELD OF THE INVENTION

The invention relates generally to annular prosthetic devices and more specifically to adjustable annular prostheses for use in the surgical repair of the atrioventricular orifices.

BACKGROUND OF THE INVENTION

It is well known that heart diseases may result in disorders of the cardiac valves. For example, diseases such as rheumatic fever can cause the shrinking or pulling apart of the valve orifice, while other diseases may result in endocarditis, an inflammation of the endocardium or lining membrane of the heart. The resulting defects in the valves hinder the normal functioning of the atrioventricular orifices and operation of the heart. More specifically, defects such as the narrowing of the valve stenoses and/or the defective closing of a valve, referred to as valvular insufficiency, result in an accumulation of blood in a heart cavity or regurgitation of blood past the valve. If uncorrected, prolonged valvular insufficiency may cause permanent damage to the leaflets, which may eventually necessitate total valve replacement.

These defects may be associated with any of the cardiac valves. For example, if the mitral valve stenosis connecting the left auricle and the left ventricle narrows, blood will accumulate in the left auricle. Similarly, in the case of mitral insufficiency, the mitral valve does not close perfectly, and blood in the left ventricle is regurgitated past the closed mitral valve into the left auricle when the ventricle contracts.

It is known to use annuloplasty rings in the repair of diseased or damaged atrioventricular valves that do not require replacement. The annuloplasty ring provides support for the mitral or tricuspid annulus and restricts expansion of the annulus or portions of the annulus to preset limits. A variety of annuloplasty rings have been employed, ranging from rigid rings of fixed size to flexible rings with a degree of adjustability. Obviously, annular prostheses that are of fixed size must be carefully selected and skillfully sutured in place. Even then, the functional result can be verified only at the end of the operation. Thus, an imperfect fit may greatly increase the duration of an operation or require corrective surgery to replace the improperly sized prosthesis.

U.S. Pat. No. 4,042,979 discloses an adjustable annular valvuloplasty ring which is said to overcome some of the problems associated with non-adjustable prostheses. The embodiment disclosed includes a frame that is sized and shaped to extend about a significant portion of the circumference of the orifice, an expandable member extending from the ends of the frame, and means for expanding and contracting the expandable member whereby segments of the ring and, accordingly, the segment shape of the orifice may be adjusted after implantation. U.S. Pat. No. 4,290,151 also discloses an adjustable annular prosthesis comprising a tubular body having a single flexible filiform string that is undulated with retention points that differentiate zones of contraction during use of the ring. This arrangement also permits some selective adjustment of the sector of the prosthesis between the retention points and the exit points of the string. The known annuloplasty rings, however, do not provide certain characteristics that are desirable to achieve successful implantation and correction of the disorder.

OBJECTS OF THE INVENTION

It is a primary object of the invention to provide an improved annular prosthesis that may not only be readily and reliably installed but may be selectively adjusted to a desired shape at the time of an operation. Related objects are to provide an adjustable prosthesis that is durable and compatible and retains the adjusted shape to increase the long-term safety and effectiveness of the prosthesis.

SUMMARY OF THE INVENTION

In accomplishing these objectives in accordance with the invention, there is provided an annuloplasty ring of a tubular construction. The tubular fabric is stitched through the mid-section of its cross section to create two parallel channels so that the cross section of the tube has essentially the shape of an "8." Colored lines along the top and bottom of the ring and coinciding with the stitch line identify the line of division between the channels. The inner channel carries two drawstrings, each of which passes completely around the ring through the inner channel, with the opposite ends of each emerging from the channel at adjacent exit points. Each of the drawstrings is anchored at two points around the circumference of the ring, such that they effectively define adjustable and fixed zones. The drawstrings may be individually and selectively tightened to reduce the arcuate length of the adjustable zones to provide a highly adjustable orifice shape. The outer channel serves as a sewing flange for implantation.

Utilizing more than one drawstring greatly increases the adjustability of the ring as well as its safety and effectiveness in that the ring will tend to retain its shape even if one of the drawstrings becomes loose or fails for some other reason. Further, as the drawstrings are continuous about the ring, the ring will exhibit greater drawstring longevity in that failure of an anchor point will not result in complete failure of a drawstring to control the size and shape of the ring. Additionally, when the drawstrings are separately anchored such that the respective anchor points do not coincide, but rather alternate with one another, the selective individual tightening of the ends of drawstrings provides four variably adjustable zones to provide a considerable adjustment flexibility and allow a smooth transition from the adjustable zones to the fixed zone. Thus, the invention provides a highly effective prosthesis that may be finely and accurately adjusted to a desired shape at the time of the operation. Further, the ring is exceptionally durable inasmuch as it will retain the adjusted shape over a long term even if one of the drawstrings should fail.

Inasmuch as the ring clearly identifies the division between the inner drawstring-carrying channel and the outer sewing flange channel, the surgeon can easily determine visually whether the ring is properly disposed. Furthermore, this clear separation of the channels minimizes the possibility of the surgeon sewing through the drawstring-carrying channel during implantation and possibly impairing the movement of the drawstrings through the channel. As a result, the invention minimizes implantation-related complications.

These and other features and advantages of the invention will be more readily apparent from reading the following description of a preferred exemplified embodiment of the invention and upon reference to the accompanying drawings wherein:

BRIEF DESCRIPTION OF THE DRAWINGS

FIG. 1 is a plan view of annuloplasty ring constructed in accordance with the invention;

FIG. 2 is a plan view, partially cut away, of the linear tube material prior to the formation into a ring of FIG. 1;

FIG. 3 is an enlarged fragmentary view of the ring of FIG. 1;

FIG. 4 is an enlarged, perspective, fragmentary view of a cross-section of the ring of FIG. 1;

FIG. 5 is an enlarged fragmentary top view of an anchor point of one of the drawstrings; and FIG. 6 is an enlarged side view of the anchor point of the drawstring as shown in FIG. 5.

DETAILED DESCRIPTION OF THE PREFERRED EMBODIMENTS

While the invention will be described and disclosed in connection with certain preferred embodiments and procedures, it is not intended to limit the invention to those specific embodiments. Rather, it is intended to cover all such alternative embodiments and modifications as fall within the spirit and scope of the invention as defined in the appended claims.

Turning now to the drawings, FIG. 1 shows a plan view of the annuloplasty ring 10 of the present invention. The ring 10 comprises a tube 12 (also shown in FIG. 2) having the ends 14, 16 joined by stitching or other joining means to form the ring 10. In order to provide a means by which the ring 10 may be adjusted to a desired shape, drawstrings 18, 20 are disposed within the tube 12 with the ends 22, 24, 26, 28 extending from the tube 12 at openings 30, 32. As discussed in more detail below, during implantation the ring 10 is sutured in place about a valve orifice, and the drawstrings 18, 20 are tightened to adjust the ring 10 to a desired shape.

In a preferred embodiment, the tube 12 is made from a knitted polyester fabric, although the tube 12 may alternately be fabricated from a Dacron (polyethylene terephthalate), double velour or other suitable fabric that optimizes tissue ingrowth. In order to further optimize tissue ingrowth, the fabric may be formed in a ribbed fashion, as shown in FIG. 3.

To minimize complications associated with the implantation of the ring 10, the cross section of the tube 12 is divided into two separate channels 34, 36. As shown in detail in the perspective cross-sectional view of FIG. 4, the tube 12 is crimped together along a longitudinally extending line 38 so that it resembles the shape of an "8" when viewed in cross section. It will be appreciated that the utilization of a single tube 12 rather than two tubes tacked together greatly reduces the formation of thrombotic voids. Further, the utilization of a single tube 12 results in a more uniform load distribution in the fabric as well as a stronger and more intimately connected ring 10. In addition, so that the tacking will only slightly reduce the elasticity of the material, the tube 12 may be tacked or stitched together with a number of separate periodic stitches 40, rather than with continuous stitching, which might result in a substantial reduction of elasticity.

The inner channel 34 houses the drawstrings 18, 20, while the outer channel 36 forms a flange, which is used to sew the ring 10 to the valve orifice. As shown in FIG. 4, a suture 42 may be sewn through the sewing channel 36 to secure the ring 10 to the tissue without interfering with the movement of the drawstrings 18, 20 within the channel 34. Although the exact size relationship of the channels 34, 36 may vary according to the tube 12 utilized and the intended application, in the embodiment shown, the outer flange 36 is about 60% of the combined channel 34, 36 width of the flattened tube 12.

The stitching line 38 between the two channels 34, 36 is identified along the outside of the tube 12 by a colored line 44 extending longitudinally along the top of the tube 12, and a longitudinally-extending colored line (not visible in the views shown in the figures) along the bottom of the tube 12. Although the lines 44 may be of any suitable color that clearly identifies the tacking line 38, in a preferred embodiment, the lines 44 are black and the tube 12 is white so that the channels 34, 36 are clearly distinguished. These lines assist in the fabrication of the ring 10 by identifying the location for the stitches 40. The lines also assist during implantation in that a surgeon implanting the ring 10 can quickly and accurately determine whether the ring 10 is properly situated. Further, because the colored lines clearly distinguish between the inner drawstring channel 34 and the outer sewing flange 36, the risk of the surgeon inadvertently sewing through the drawstrings 18, 20 disposed in the inner drawstring channel 34, which could prevent proper adjustment of ring 10 size by inhibiting the sliding of the drawstrings 18, 20 through the channel 34, will be greatly reduced.

Each drawstring 18, 20 extends around substantially the length of the channel 34 with the ends 22, 24, 26, 28 extending from channel 34 at openings 30, 32. In order to define zones of the ring 10 that may be selectively adjusted in order to adjust the overall size and shape of the ring 10, each of the drawstrings is anchored to the tube 12 at two different points. In the exemplified embodiment, drawstring 18 is anchored at points 46 and 48, and drawstring 20 is anchored at points 50 and 52. The drawstrings 18, 20 may be anchored by any suitable method that is secure and permanent. In the embodiment shown in the top and side view of FIGS. 5 and 6, respectively, a knot is formed in the drawstring 18, 20 through and around the material of the tube 12 via various entry and exit points.

Returning now to FIG. 2, it will be appreciated that anchor points 48 and 50 will define a fixed zone therebetween that is flexible, yet neither contractible nor extensible by action of the drawstrings, while the zones between anchor point 50 and opening 30, and between anchor point 48 and opening 32, will be adjustable by tightening the ends 22, 24, 26, 28 of the drawstrings 20, 18, respectively. Although the exact location of the anchor points 46, 48, 50, 52 may vary depending upon the size of the ring 10 and the other factors affecting optimization, in the preferred embodiment of the invention depicted in FIG. 1, the angle "A" between the two inner anchor points 48, 50 is approximately 90° and the angle "B" between the two outer anchor points 46, 52 is approximately 150°.

It will be appreciated that once the ring 10 has been sutured in place during implantation, the annulus may be reduced symmetrically or asymmetrically by pulling one or more of the four drawstring ends 22, 24, 26 or 28 extending from the ring 10. It may be desirable to tie only a releasable knot in the drawstring, and then test the repair before securing the drawstring 18 knot more permanently. Once it has been determined that the repair is satisfactory, the drawstring knot may be more permanently secured. In order to provide additional adjustability, as well as additional strength and redundant safety in the event that the primary drawstring 18 fails due to suture needle damage or knot failure, the other drawstring 20 may be tightened as appropriate and tied off. In this regard, it will be appreciated that drawstrings 18 and 20 may be used to "fine-tune" or otherwise tailor the annulus shape in the adjustable zones between anchor points 48, 50 and the openings 32, 30, respectively.

In summary, the invention provides an adjustable annuloplasty ring 10 of a tubular construction that is fabricated by joining the ends of a tube 12 that has been stitched through the mid-section of its annular cross section to create two parallel channels 34, 36. The inner channel 34 carries two drawstrings 18, 20, which pass completely around the channel 34 and are each anchored at two different points 46, 48, 50, 52, for adjusting the size of the ring 10. The outer channel 36 is used as a sewing flange to suture the ring 10 in place when implanted. Because the line of stitching 38 through the tube 12 is marked on the top and bottom of the tube 12 with a colored line 40, implantation-related complications are minimized in that the surgeon can easily determine if the ring 10 is properly located and identify the outer sewing flange channel 36. Further, the dual drawstring arrangement greatly increases the adjustability, safety and effectiveness of the ring 10.

We claim as our invention:

1. An adjustable annuloplasty ring for an orifice, comprising:
    a flexible fabric tube formed in the shape of a ring,
    means for dividing the tube into an inner channel and an outer channel which functions as a sewing flange by which the ring may be sutured to tissue surrounding the orifice,
    at least two drawstrings for adjusting the size and shape of the ring disposed in the inner channel, the drawstrings extending substantially around the circumference of the ring and having ends protruding from openings in the tube, each drawstring being coupled to the tube at least two separate anchor points,
    whereby the size and shape of the ring may be adjusted by selectively tightening one or more ends of the drawstrings to constrict portions of the ring.

2. An adjustable annuloplasty ring as claimed in claim 1 wherein the anchor points of the drawstrings alternate around the circumference.

3. An adjustable annuloplasty ring as claimed in claim 2 comprising two drawstrings and wherein the two adjacent anchor points opposite the openings for the drawstring ends are on the order of approximately 90° apart and the two outermost anchor points are on the order of approximately 150° apart.

4. An adjustable annuloplasty ring as claimed in claim 1 wherein the tube is made from a knitted polyester fabric.

5. An adjustable annuloplasty ring as claimed in claim 1 wherein the means for dividing the tube is periodic stitching.

6. An adjustable annuloplasty ring as claimed in claim 1 further comprising at least one colored identification line along the division between the inner and outer channels.

7. An adjustable annuloplasty ring as claimed in claim 1 wherein the width of the outer channel is on the order of approximately 60% of the flattened tube width.

8. An adjustable annuloplasty ring for an orifice, comprising:
    a flexible fabric tube formed in the shape of a ring,
    means for dividing the tube into an inner channel and an outer channel which functions as a sewing flange by which the ring may be sutured to tissue surrounding the orifice,
    at least one drawstring slidably disposed within the inner channel whereby the size and shape of the ring may be adjusted, and suturing the tube through the outer channel does not interfere with the adjustment of the ring by the drawstring.

9. An adjustable annuloplasty ring as claimed in claim 8 wherein the tube is made from a knitted polyester fabric.

10. An adjustable annuloplasty ring as claimed in claim 8 wherein the means for dividing the tube is periodic stitching.

11. An adjustable annuloplasty ring as claimed in claim 8 further comprising at least one colored identification line along the division between the inner and outer channels.

12. An adjustable annuloplasty ring as claimed in claim 8 wherein the width of the outer channel is on the order of approximately 60% of the flattened tube width.

13. An adjustable annuloplasty ring for an orifice, comprising:
    a flexible fabric tube formed in the shape of a ring,
    at least two drawstrings for adjusting the size and shape of the ring slidably disposed in the tube, the drawstrings extending substantially around the circumference of the ring and having ends protruding from openings in the tube, each drawstring being secured to the tube at least two separate anchor points,
    whereby the size and shape of the ring may be adjusted by selectively tightening one or more ends of the drawstrings to constrict portions of the ring.

14. An adjustable annuloplasty ring as claimed in claim 13 wherein the anchor points of the drawstrings alternate around the circumference.

15. An adjustable annuloplasty ring as claimed in claim 14 comprising two drawstrings and wherein the two adjacent anchor points opposite the openings for the drawstring ends are on the order of approximately 90° apart and the two outermost anchor points are on the order of approximately 150° apart.

16. A method of supporting and constricting an orifice utilizing an adjustable annuloplasty ring having a flexible tube formed in the shape of a ring, at least two drawstrings extending around the circumference of and slidably disposed in the tube and having ends protruding from openings in the tube, each drawstring being anchored to the tube at least two points alternating around the circumference of the ring, comprising the steps of:
    securing the ring about the orifice,
    independently tightening and securing the four drawstring ends to adjust the ring to a desired shape.

* * * * *